(12) United States Patent
Ruth (10) Patent No.: US 7,454,951 B2
(45) Date of Patent: Nov. 25, 2008

(54) GAS SENSOR

(75) Inventor: Juergen Ruth, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 304 days.

(21) Appl. No.: 11/323,709

(22) Filed: Dec. 29, 2005

(65) Prior Publication Data

US 2006/0162423 A1 Jul. 27, 2006

(30) Foreign Application Priority Data

Dec. 29, 2004 (DE) .................. 10 2004 063 173

(51) Int. Cl.
G01N 7/00 (2006.01)
(52) U.S. Cl. .................................... 73/23.31
(58) Field of Classification Search .............. 73/23.31
See application file for complete search history.

(56) References Cited

U.S. PATENT DOCUMENTS

| | | | |
|---|---|---|---|
| 6,415,647 B1 * | 7/2002 | Yamada et al. ............. 73/31.05 |
| 6,546,783 B2 * | 4/2003 | Shirai .......................... 73/31.05 |
| 6,672,132 B1 * | 1/2004 | Weyl et al. .................. 73/23.31 |
| 6,758,082 B2 * | 7/2004 | Geier et al. ................. 73/31.05 |
| 6,851,180 B2 * | 2/2005 | Hattori et al. .................. 29/619 |
| 6,898,961 B2 * | 5/2005 | Yamada et al. ............. 73/31.05 |
| 6,997,038 B2 * | 2/2006 | Kojima ....................... 73/23.31 |
| 7,021,354 B2 * | 4/2006 | Kobayashi et al. ........... 156/351 |
| 7,168,295 B2 * | 1/2007 | Yamauchi et al. .......... 73/31.05 |
| 7,181,840 B2 * | 2/2007 | Yamada et al. ................ 29/857 |
| 7,211,222 B2 * | 5/2007 | Satou et al. .................... 422/83 |
| 2003/0061862 A1 * | 4/2003 | Kondo et al. ............... 73/23.31 |
| 2005/0028581 A1 * | 2/2005 | Tsuji ........................... 73/31.05 |

FOREIGN PATENT DOCUMENTS

| | | |
|---|---|---|
| DE | 41 26 378 | 4/1992 |
| DE | 198 03 334 | 8/1999 |
| DE | 101 35 235 | 2/2003 |

* cited by examiner

Primary Examiner—Hezron E. Williams
Assistant Examiner—Rodney T Frank
(74) Attorney, Agent, or Firm—Kenyon & Kenyon LLP (57) ABSTRACT

A sealing device encloses a range of a base area and/or a cover area of a sensor element, which is accessible through an opening developed in a housing. Because of this, a seal may be achieved between the measured gas region and the reference gas region of the gas sensor, that is constructed using comparatively few individual parts, and, accordingly, also requires fewer method steps in its manufacture and assembly.

11 Claims, 8 Drawing Sheets

GAS SENSOR

FIELD OF THE INVENTION

The present invention relates to a gas sensor, especially for determining the oxygen content in exhaust gases of internal combustion.

BACKGROUND INFORMATION

Two such gas sensors may be seen in two German Patent Application Nos. DE 41 26 378 and DE 198 03 334 that originate from the same applicant. These two gas sensors are constructed from a plurality of individual parts, that have to be fit together with a corresponding expenditure. The manufacturing costs for such gas sensors are, consequently, among other things, besides being a function of the number of component parts, also a function of the required number of manufacturing steps.

SUMMARY OF THE INVENTION

Therefore, the present invention is based on the object of reducing the cost of manufacturing such gas sensors. The present invention relates to a gas sensor, especially for determining the oxygen content in exhaust gases of internal combustion engines. A crux of the present invention is that a seal encloses a range of a surface, preferably a base area or a cover area of the sensor element, which is accessible through an opening developed in the housing.

Because of such a sealing design, it is possible, using only one sealing element, to separate a large planar region of the sensor element from the measured gas region of the gas sensor. The seal, in this context, may be established together with the sensor element, in both a sealing and a fixing manner, in a single method step, by compression molding of the housing. To accomplish this, neither additional fixing elements nor further method steps are required for their production or for mounting them.

An additional advantage of this sealing device is that this sensor region is easily accessible for carrying out additional processing steps, even after sealing takes place, which may be attributed especially to the fact that the opening in the housing is designed transversely to the longitudinal extension of the sensor element. Thus, the sensor element may be contacted, for instance, on the inside, directly at the printed circuit traces, the type of contacting even being freely selectable within the scope of the given connecting possibilities. Contact surfaces situated at the surface of the sensor element, that were required up to this time, for the connecting wires leading to the outside, the so-called contact pads, may consequently be omitted.

In such a design, it is also possible to situate the seal about several connecting contacts, in common, of the sensor element and/or about one or more connecting contacts individually. An additional cost reduction comes about by doing without separately developed sealing elements, particularly if these sealing elements are situated at the sensor element using a single additional method step in producing the sensor element that is preferably constructed in a planar manner.

In order to be able to automate even better the production sequence when assembling the gas sensor, in one advantageous refinement it may be provided that the seal is developed in several parts, so that a sensor fixing element is situated between a part of the seal on the sensor side and a part of the seal that is on the housing side. Therewith it is possible, for example, to situate the seal in the housing together with this sensor fixing element, and, if necessary, to already wire the contact elements of the connecting lines, so that the entire unit may be prefabricated, and has subsequently still only to be automatically equipped with the sensor element and compression molded.

In this case it is particularly advantageous if a positioning aid and/or a fixing aid is situated on the seal. If the seal is additionally developed electrically or insulating with respect to heat technology, this has a further positive effect on the fixing and contacting of the sensor element in the housing. Especially at high temperatures, at which various alloys become electrically conductive, interferences in the transmission of electrical signals may be reduced or even completely avoided by using insulatingly fixed contacts.

However, besides the embodiment of the seal that is directly printed onto the sensor element, it may also be advantageous to provide such a device as a separately developed insertion part. This is particularly of advantage if additional positioning and/or fixing elements are provided for the sensor element in the housing. In that case, for example, a sealing element developed as a separate part may be inserted between such a positioning element and/or fixing element and the housing. Of course, it is also possible to develop the seal in common with the positioning and/or fixing element as one unit, which, in turn, again has a positive effect on the method sequence during assembly.

Preferably, the seal is made of a ductile material, so that it is able to take up the forces occurring during the compression molding of the housing, and, at the same time, fix the sensor element in a sealing manner.

It is regarded as being particularly preferred if the seal, or at least a part of the seal, is made of fused material. Thus, a gas-tight connection may be developed between a metallic and a ceramic substrate, such as the one according to the technical teaching of German Patent Application No. DE 101 35 235, in order to connect the sensor element that is, as a rule, made of ceramic to a metallic housing in a gas-tight manner. In this case, no additional sealing elements are required, and the fixing of the sensor element is done without any deformation whatsoever of the adjacent material regions. This is possible especially when using a laser beam, which heats mutually bordering materials possibly with, or even without additionally required solder glass and fuses them with each other.

Using a seal developed in such a way, additional method steps may be omitted, such as those for manufacturing, storing and assembling sealing and/or fixing elements that are thereby omitted.

DETAILED DESCRIPTION

Figure 1:
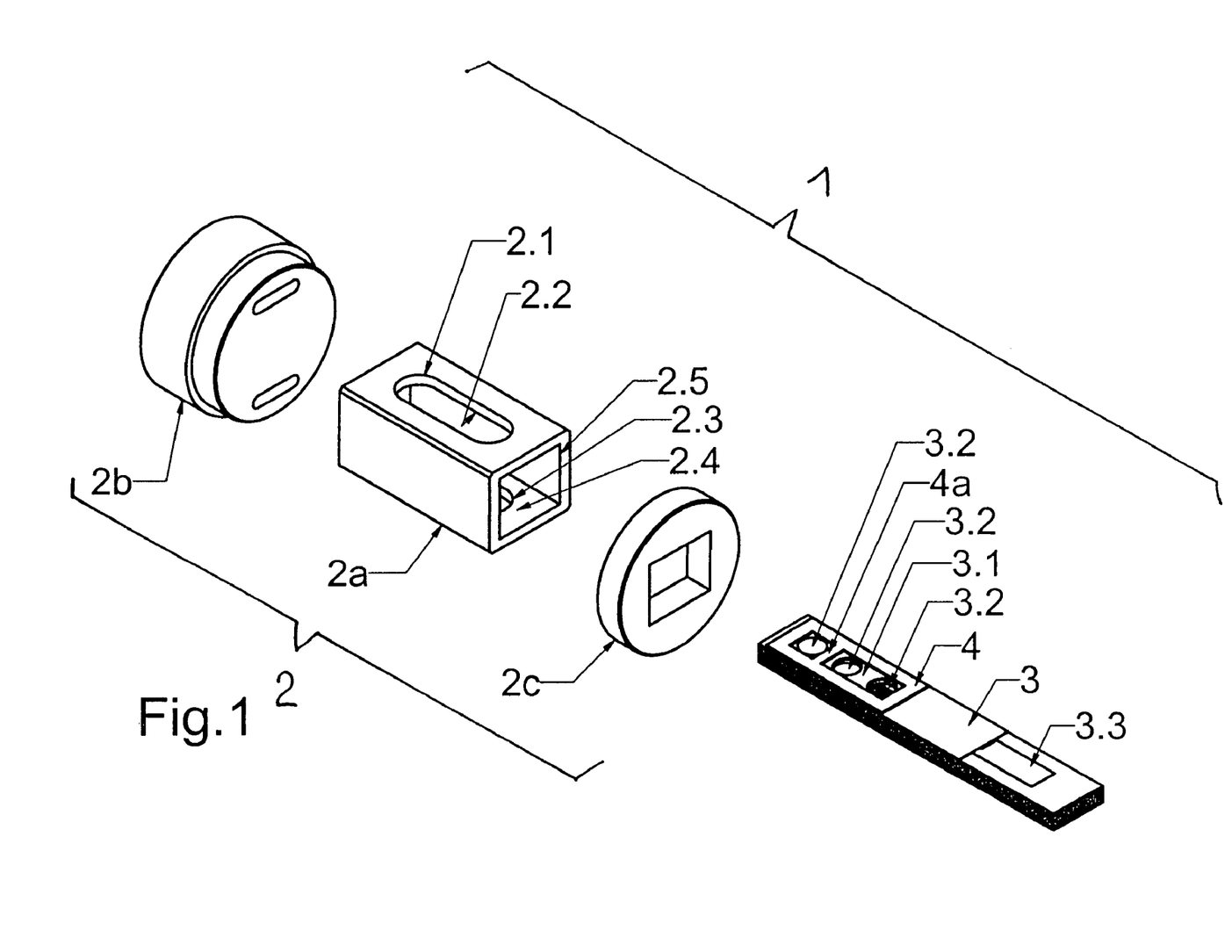
FIG. 1 shows a top view, at an angle, showing a housing, pulled apart in an exploded manner, of a gas sensor having a sensor element that is to be fitted into it, and a sealing device according to the present invention.

FIG. 1 shows a top view, at an angle, onto a gas sensor having components 2 to 4 that are shown pulled apart in an exploded manner. For an improved representation of the individual details, housing parts 2a through 2c are also shown in an exploded manner.

Housing part 2a has an opening 2.1 in its wall that is directed upwards, which makes possible access to inner space 2.5 of housing 2. On the inside of this wall, and around opening 2.1, a sealing region 2.2 is defined for the sealing device according to the present invention. For the flexible use of the housing, an additional opening 2.3 is developed at the wall of housing part 2a lying opposite the first opening, to which, according to the present invention, a corresponding sealing region 2.4 is assigned.

At a sensor element 3, situated in front of housing 2, a seal 4 mounted on the former is shown. When sensor element 3 is fixed, this sealing device is pressed against sealing region 2.2 on the inside of housing 2, so that there is created a gas-tight separation between the measured gas region and the reference gas region of the gas sensor. Additional fixing elements may be provided for fixing sensor element 3 in housing 2, which, however, have not been shown here, for simplicity's sake.

Seal 4, situated at sensor element 3, consequently separates a region of a base area and/or cover area of the sensor element from the remaining part of the sensor element that is exposed to the measuring gas. It forms the sensor element part, that is assigned to the reference region of the gas sensor, which is accessible via opening 2.1 that is developed transversely to the longitudinal extension of the sensor element, even after the sensor element is fixed. Consequently, the seal encloses several connecting contacts 3.2, which are developed in common in contact region 3.1. For the separation of an individual contact, for instance, in this case, a sealing crosspiece 4a is shown between adjoining sections of seal 4 that run in the longitudinal direction.

Figure 2:
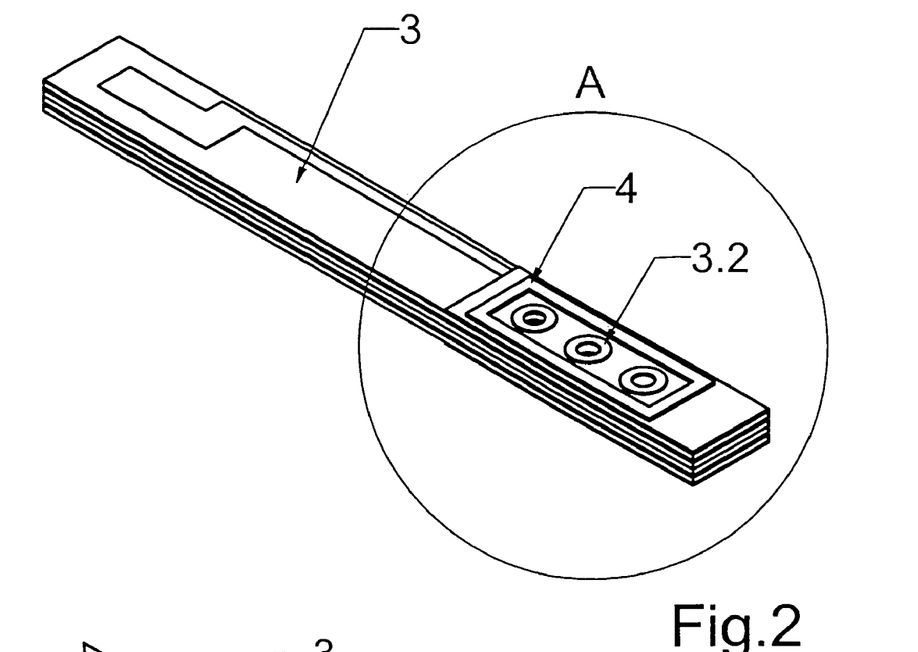
FIG. 2 shows a sensor element having a sealing device according to the present invention.
Figure 2A:
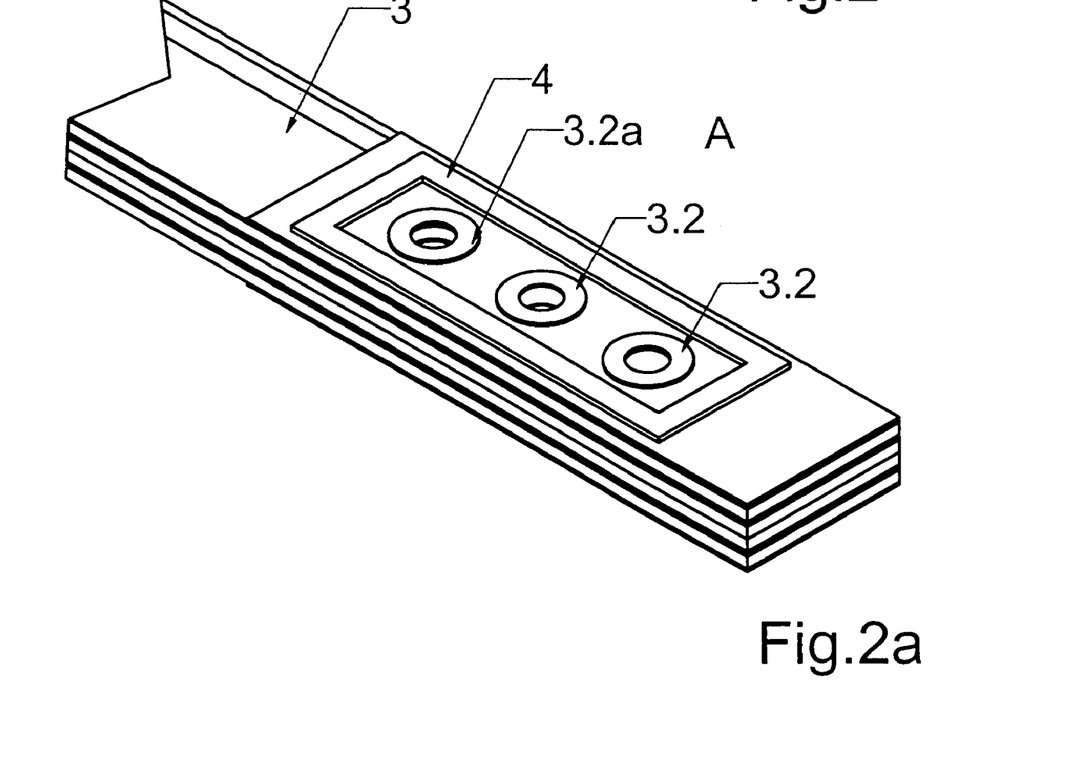
FIGS. 2a, 2b and 2c show an enlarged representation of the sealing region from FIG. 2 (FIG. 2a) and specific embodiments modified from these (FIGS. 2b, 2c).
Figure 2B:
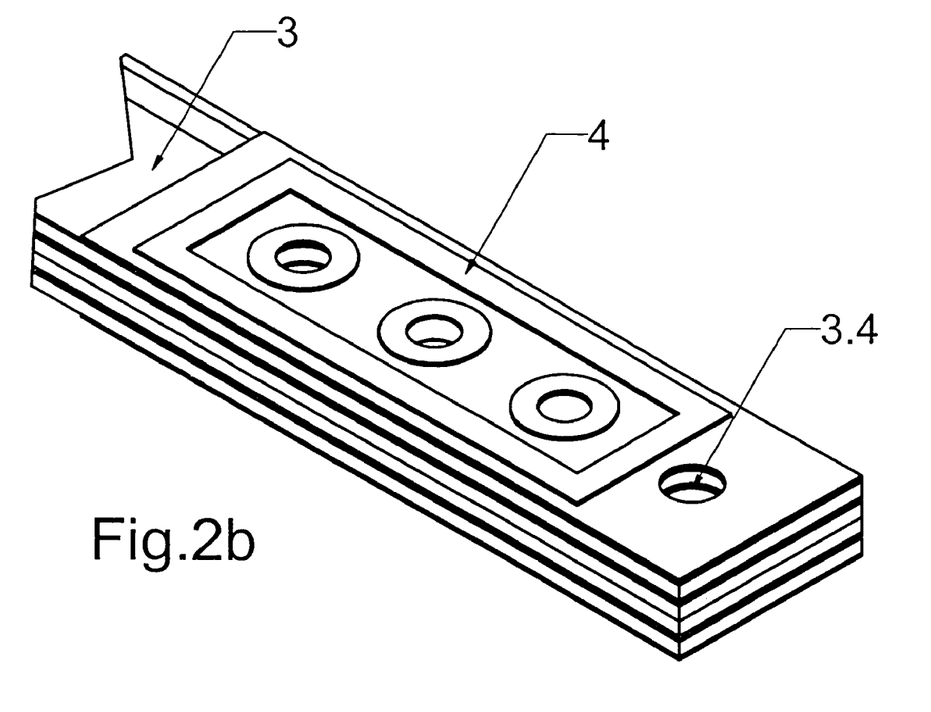
Figure 2C:
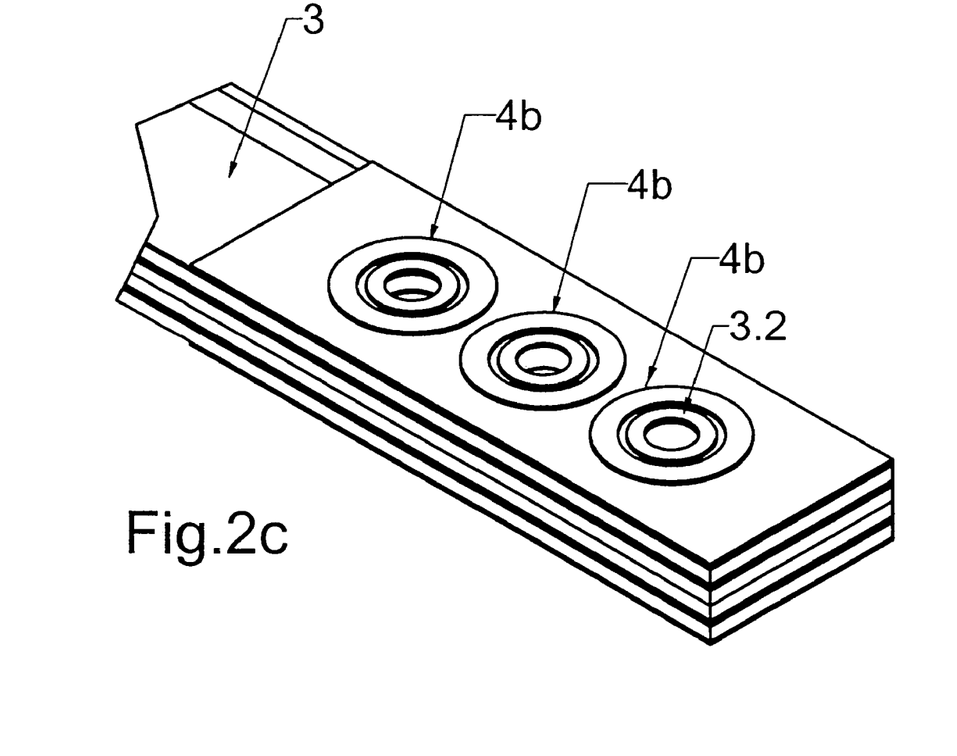

Various modifications of this specific embodiment of the sealing device according to the present invention are shown in FIGS. 2 through 2c. FIG. 2 shows a sensor element 3 having a first specific embodiment of a seal 4 according to the present invention, without an additional sealing crosspiece 4a. FIG. 2a shows an enlarged cutout A from the illustration in FIG. 2. In this case, it may be recognized that contact 3.2a has, in addition, an access to the reference gas channel on the inside of the sensor element.

FIG. 2b has a specific embodiment modified from the latter, which, in addition, has a hole-like positioning aid and/or fixing aid 3.4. This, together with a further element that engages in the opening, may form an ensurance against loss for the sensor element. Because of this, even if there is a possibly abating clamping effect of the housing on the sensor element, the sensor element is no longer able to slip out of it.

This makes it increasingly certain that equipment positioned downstream in the exhaust gas plant, such as a catalyst, is protected from damage due to a lost sensor element.

FIG. 2c shows another specific embodiment of a sealing device according to the present invention on a sensor element 3 in a cutout-like, enlarged illustration. In this case, seal 4 is made up of three separately developed sealing elements 4b, that are in each case situated around a connecting contact 3.2. For this specific embodiment, the housing has correspondingly developed openings, which also make possible access to the contacts.

Figure 3:
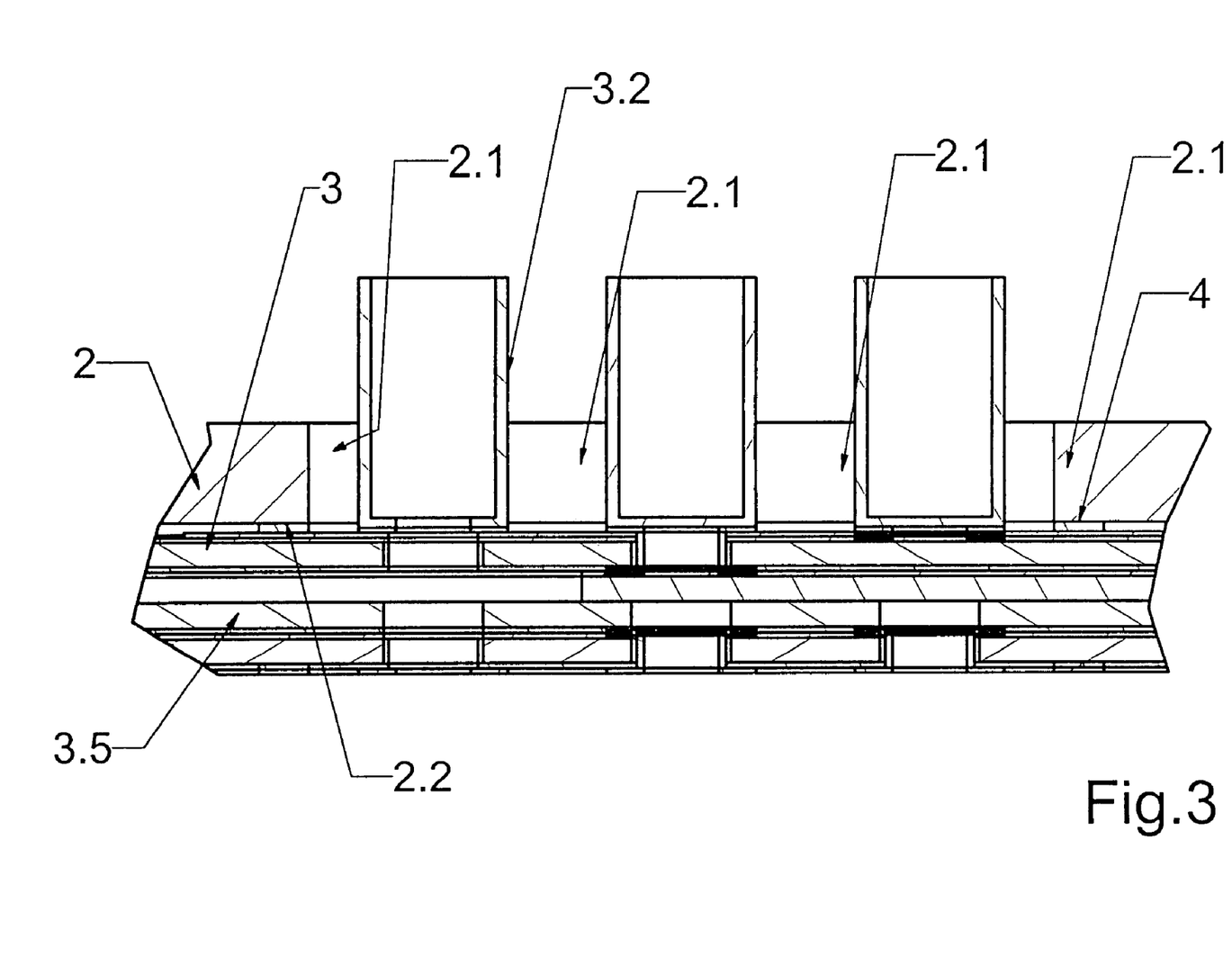
FIG. 3 shows a cut out sectional representation through a housing having a sensor element set into it and a seal according to the present invention.

FIG. 3 shows the sectioned representation of a housing part 2, a sensor element situated in it, and a seal 4, according to the present invention, of a gas sensor 1.

From the base area or the cover area of sensor element 3, a connecting contact 3.2 extends through opening 2.1, all the way through the housing, to the outside. It is located in the region of the gas sensor that is on the reference gas side, and that is separated from the region of the measuring gas side by seal 4 in the housing. Reference gas channel 3.5 also opens out in the area of opening 2.1.

In order to attain a clean pressure distribution during the compression molding of the housing for the fixing of sensor element 3, a seal 4 is also situated between the back side of the sensor element and the inner side of housing 2 that is assigned to it. Because of that, point-by-point occurring force applications may be distributed over such large areas that they are not problematical for the ceramic sensor element.

Figure 4:
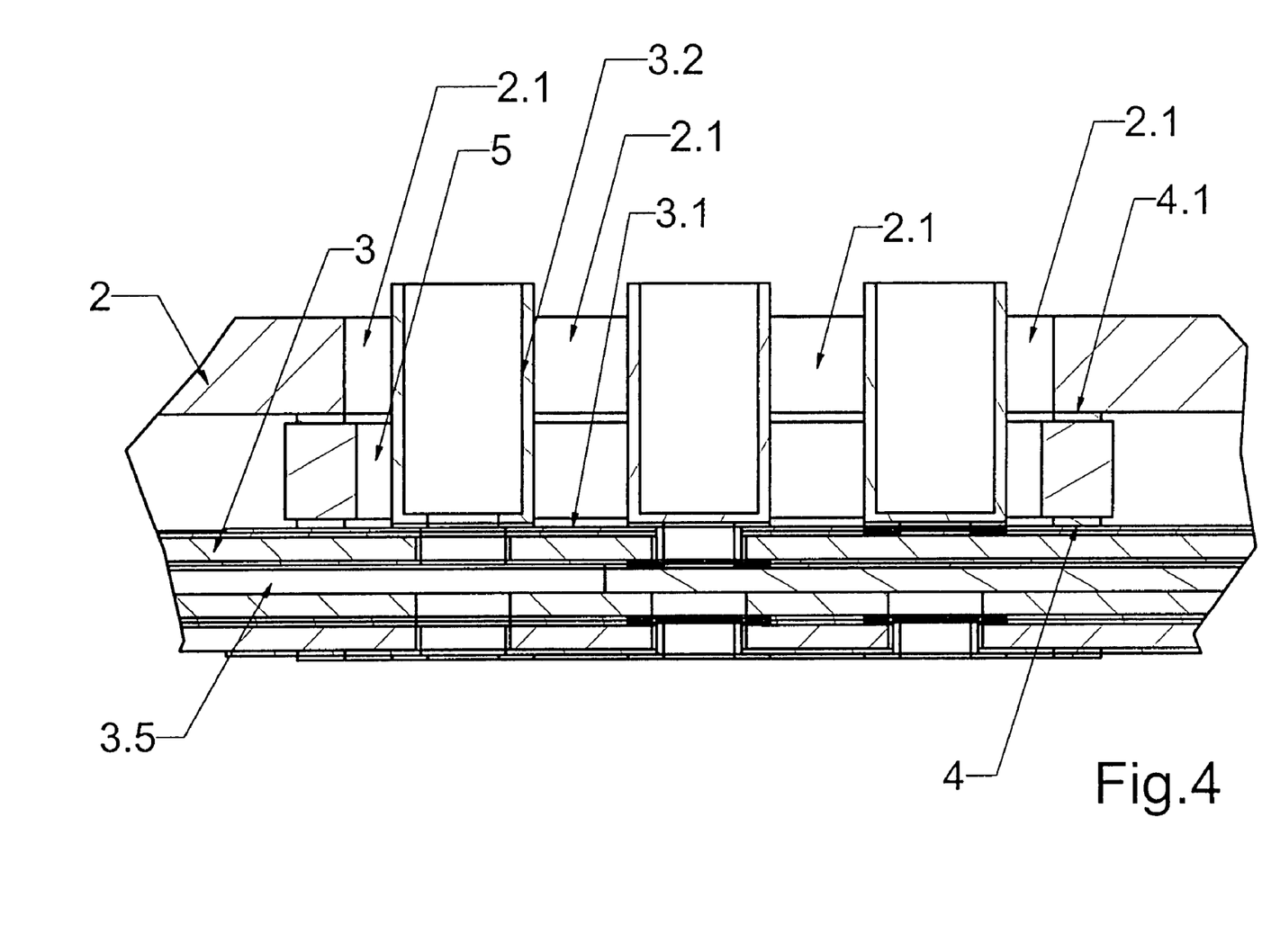
FIG. 4 shows a specific embodiment modified from FIG. 3.
Figure 5:
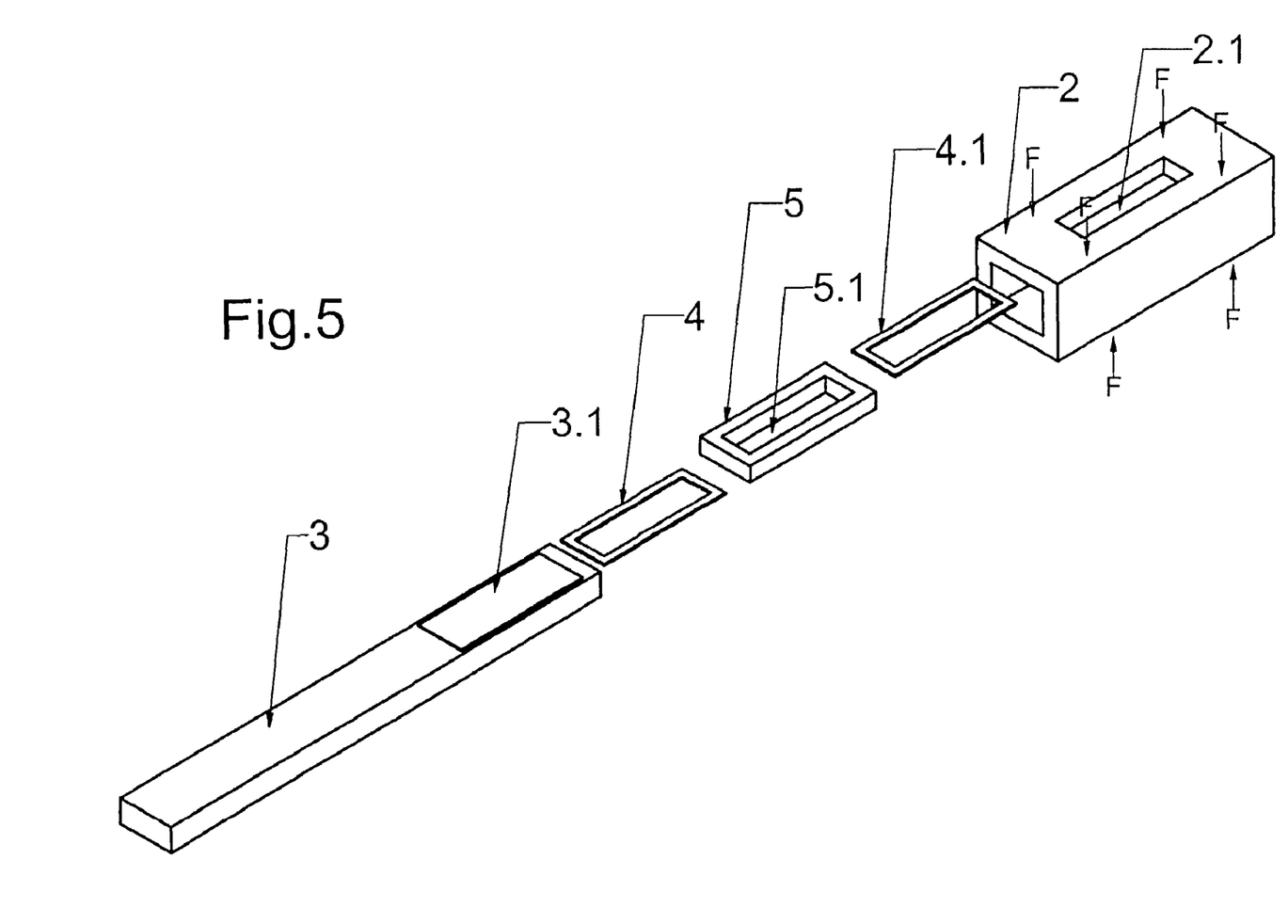
FIG. 5 shows a top view, at an angle, showing a sensor element housing pulled apart in an exploded manner, having a sensor element that is to be fitted into it, as well as various elements of the sealing device according to the present invention.

FIG. 4 shows a partial cutout of yet another specific embodiment of a gas sensor in a sectional illustration, which corresponds to the specific embodiment in FIG. 5. It is different from the specific embodiments up to now in that, between seal 4 and housing 2 there is situated additionally a sensor fixing element 5. An additional seal 4.1 is shown for sealing between this sensor fixing element 5 and housing 2, and situated between the two.

Figure 7:
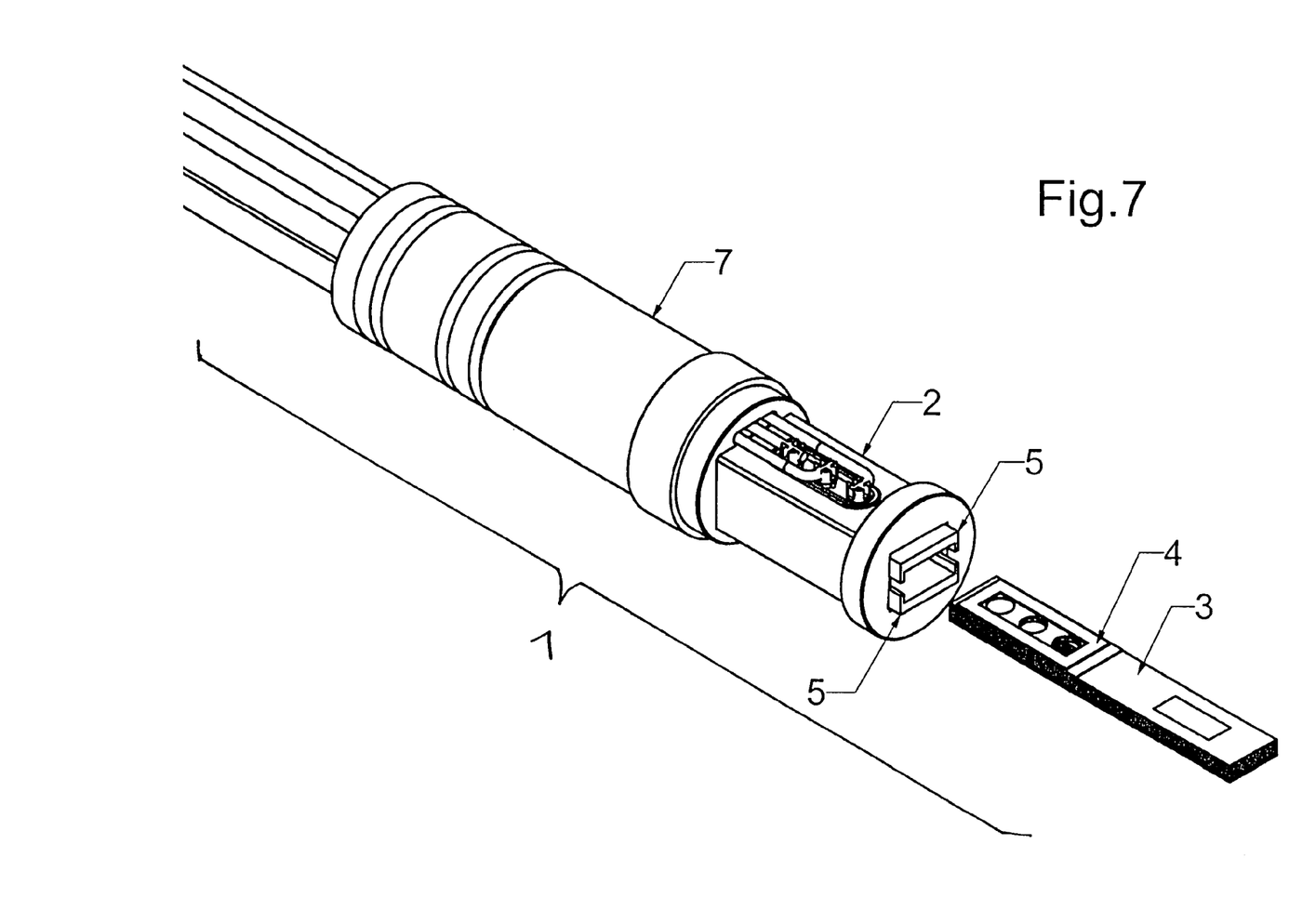
FIG. 7 shows a gas sensor housing prepared for accommodating a sensor element.

It may be advantageous for the assembly of the gas sensor that sensor fixing element 5 is situated together with additional seal 4.1 in housing 2. Furthermore, as shown in FIG. 7, contact elements of the electrical lines leading to the outside may additionally be pre-positioned through opening 2.1. Of course, to do this, additional gas sensor elements are required, using which, cable harness 7 may be correspondingly connected to housing 2, so that finally only sensor element 3 has still to be inserted into the housing that has been thus prepared, and compression molded. Opening 5.1 in sensor fixing element 5 corresponds, as far as size is concerned, to opening 2.1 in the housing, and encloses contact region 3.1 of sensor element 3, so that the latter is separated from the measuring gas region in a gas-tight manner.

Figure 6:
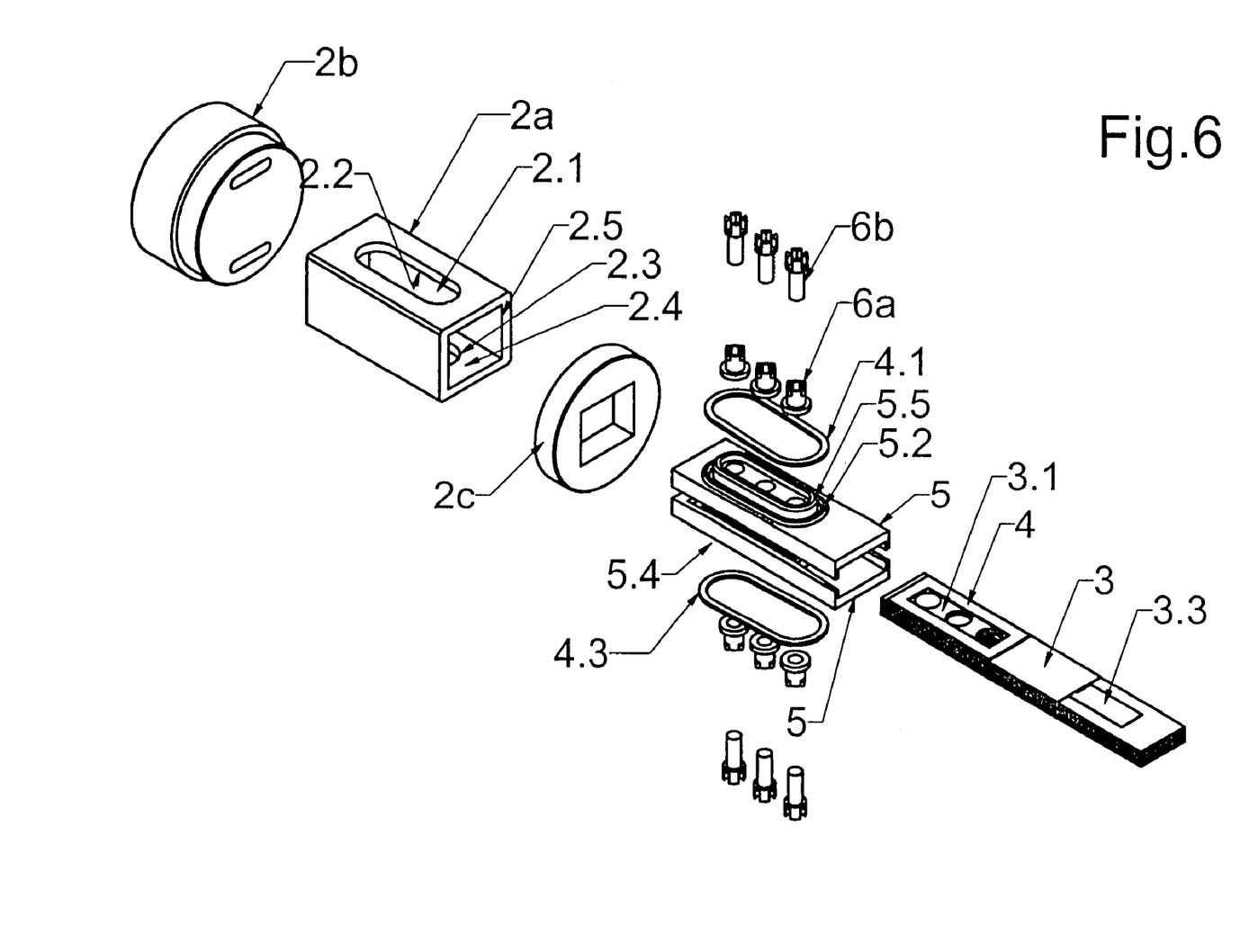
FIG. 6 shows a specific embodiment as in FIG. 1, however, having an additionally situated positioning and/or fixing element.

FIG. 6 shows a specific embodiment of the gas sensor, which builds up on the specific embodiment of FIG. 1, and which is broadened by the elements additionally shown in FIGS. 4 and 5. The installation of sensor element 3 in housing 2, as has been explained, takes place by prefabricating the entire accommodation unit housing 2, sensor fixing element 5 and contacts 6 together with cable harness 7 that is attached to them. Subsequently, only sensor element 3 has still to be pushed into the remaining opening of sensor fixing element 5 positioned on the inside of the housing, and fixed in a gas-tight manner by compression molding of the housing.

In this case, sensor fixing element 5 is to be assigned functionally to seal 4, since that is also developed in a gas-tight manner. Consequently, seal 4 is developed as a plurality of parts, and has a positioning aid and/or a fixing aid together with the collar that is situated in seal 4.1 and extends into opening 2.1. For sealing from the housing, seal 4.1 lies on top of sealing region 5.2. In order to be able, using the same housing, to accommodate a sensor element that has corresponding connectors also at the opposite base area, both the housing and sensor fixing element 5 are preferably developed in a symmetrical fashion.

FIG. 7 shows a prefabricated, assembled housing 2 having sensor element fixing 5 inserted into it and cable harness 7 connected to contacts 6. It only has to be still equipped with sensor element 3 and compression molded for fixing the latter.

LIST OF REFERENCE NUMERALS

1 gas sensor
2 housing
3 sensor element
4 seal
5 sensor fixing element
6 contacts
7 cable harness
2.1 opening
2.2 sealing region
2.3 opening
2.4 sealing region
2.5 innerspace
3.1 contact region
3.2 connecting contact
3.3 measured gas electrode
3.4 positioning aid
3.5 reference gas channel
4.1 seal
4.2
4.3 seal
4.4
4.5
4*a* sealing crosspiece
4*b* seal
5.1 opening
5.2 sealing region
5.3
5.4 sealing region
5.5 positioning aid and/or fixing aid

What is claimed is:

1. A gas sensor comprising:
a housing;
a sensor element situated in the housing; and
a seal situated between the housing and the sensor element for delimiting a reference gas region from a measured gas region, the seal enclosing a range of an area of the sensor element, the range of the area of the sensor element being accessible through an opening situated in the housing;
wherein the seal is situated around a plurality of connecting contacts of the sensor element, at least one of (a) in common and (b) around at least one of the connecting contacts individually.

2. The gas sensor according to claim 1, wherein the opening in the housing is developed transversely to a longitudinal extension of the sensor element.

3. The gas sensor according to claim 1, wherein the area enclosed by the seal is at least one of a base area and a cover area of the sensor element.

4. The gas sensor according to claim 1, wherein the seal has a multi-part design.

5. The gas sensor according to claim 1, further comprising a sensor fixing element situated between a part of the seal on a side of the sensor element and a part of the seal on a side of the housing.

6. The gas sensor according to claim 1, further comprising at least one of a positioning aid and a fixing aid situated on the seal.

7. The gas sensor according to claim 1, wherein the seal is developed at least one of electrically and insulating in a heat technological manner.

8. The gas sensor according to claim 1, wherein the seal is a separately developed insertion part.

9. The gas sensor according to claim 1, wherein the seal is made of a ductile material.

10. The gas sensor according to claim 1, wherein the seal is made of a fused material.

11. The gas sensor according to claim 1, wherein the gas sensor is for determining an oxygen content in exhaust gases of an internal combustion engine.

* * * * *